United States Patent
Shohat et al.

(10) Patent No.: US 12,295,580 B2
(45) Date of Patent: May 13, 2025

(54) SYSTEMS, DEVICES, AND METHODS FOR ADJUSTING BLOOD FLOW IN A BODY LUMEN

(71) Applicant: Revamp Medical Ltd., Netania (IL)

(72) Inventors: Yael Shohat, Herzliya (IL); Ofer Razi, Tel Aviv (IL); Lihu Avitov, Tel Aviv (IL); Raphael Benary, Tel Aviv (IL)

(73) Assignee: REVAMP MEDICAL LTD., Netania (IL)

( * ) Notice: Subject to any disclaimer, the term of this patent is extended or adjusted under 35 U.S.C. 154(b) by 905 days.

(21) Appl. No.: 17/413,391

(22) PCT Filed: Dec. 11, 2019

(86) PCT No.: PCT/IL2019/051360
§ 371 (c)(1),
(2) Date: Jun. 11, 2021

(87) PCT Pub. No.: WO2020/121309
PCT Pub. Date: Jun. 18, 2020

(65) Prior Publication Data
US 2022/0061852 A1    Mar. 3, 2022

Related U.S. Application Data (60) Provisional application No. 62/777,788, filed on Dec. 11, 2018.

(51) Int. Cl.
*A61B 17/12* (2006.01)
*A61M 25/00* (2006.01)
*A61B 17/00* (2006.01)

(52) U.S. Cl.
CPC .... *A61B 17/12036* (2013.01); *A61B 17/1204* (2013.01); *A61B 17/12109* (2013.01);
(Continued)

(58) Field of Classification Search
CPC .......... A61B 17/12022; A61B 17/1204; A61B 17/12027; A61B 17/12109;
(Continued)

(56) References Cited

U.S. PATENT DOCUMENTS

| 4,710,192 A | 12/1987 | Liotta et al. |
| 5,443,477 A | 8/1995 | Marin et al. |

(Continued)

FOREIGN PATENT DOCUMENTS

| CN | 108366799 A | 8/2018 |
| EP | 2025360 A2 | 2/2009 |

(Continued)

OTHER PUBLICATIONS

Extended European Search Report for Application No. EP20190896189, mailed on Oct. 31, 2022, 13 pages.
(Continued)

*Primary Examiner* — Scott J. Medway
*Assistant Examiner* — Anh Bui
(74) *Attorney, Agent, or Firm* — COOLEY LLP (57) ABSTRACT

Embodiments of the present disclosure are directed to blood-flow regulation systems and associated methods, and, in some embodiments, includes an adjustable blood flow regulation device that includes an inner tube, an expandable member coupled to the inner tube, a proximal control handle that includes a controller operatively coupled to the member and configured to control expansion of the member, and a downstream tip member coupled to a distal portion of the inner tube which is distal to the member. The tip member is coupled to a first fluid pressure sensor. A second fluid pressure sensor is coupled to a portion of the inner tube proximal to the member.

24 Claims, 6 Drawing Sheets

(52) U.S. Cl.
CPC ... *A61B 17/12168* (2013.01); *A61M 25/0082* (2013.01); *A61B 2017/0042* (2013.01); *A61B 2017/1205* (2013.01); *A61M 2025/0002* (2013.01); *A61M 2025/0004* (2013.01); *A61M 25/0074* (2013.01); *A61M 2210/1082* (2013.01)

(58) Field of Classification Search
CPC .......... A61B 17/12136; A61B 5/02158; A61B 5/6853; A61B 2017/00022; A61M 25/0082; A61M 25/0074; A61M 25/1011; A61M 2025/0002; A61M 2025/1013; A61M 5/31586; A61M 5/31581
See application file for complete search history.

(56) References Cited

U.S. PATENT DOCUMENTS

| | | | |
|---|---|---|---|
| 5,683,451 | A | 11/1997 | Lenker et al. |
| 5,755,779 | A | 5/1998 | Horiguchi |
| 5,827,324 | A | 10/1998 | Cassell et al. |
| 6,120,534 | A | 9/2000 | Ruiz |
| 6,448,019 | B1 | 9/2002 | Mendelsohn et al. |
| 6,638,293 | B1 | 10/2003 | Makower et al. |
| 6,692,928 | B1 | 2/2004 | Mendelsohn et al. |
| 6,953,476 | B1 | 10/2005 | Shalev |
| 7,063,714 | B2 * | 6/2006 | Dorros ............. A61B 17/12136 604/523 |
| 7,935,075 | B2 | 5/2011 | Tockman et al. |
| 8,454,952 | B2 | 6/2013 | Rade et al. |
| 8,876,850 | B1 | 11/2014 | Vollmers et al. |
| 9,393,384 | B1 | 7/2016 | Kapur et al. |
| 9,468,666 | B2 | 10/2016 | Kapur et al. |
| 10,195,406 | B2 | 2/2019 | Karavany et al. |
| 10,279,152 | B2 | 5/2019 | Kapur et al. |
| 10,363,044 | B2 | 7/2019 | Tal et al. |
| 10,703,820 | B2 | 7/2020 | Kapur et al. |
| 10,758,715 | B2 | 9/2020 | Kapur et al. |
| 10,842,974 | B2 | 11/2020 | Kapur et al. |
| 10,893,927 | B2 | 1/2021 | Sohn |
| 10,926,065 | B2 | 2/2021 | Jönsson |
| 11,039,915 | B2 | 6/2021 | Tuval et al. |
| 11,160,654 | B2 | 11/2021 | Tuval |
| 11,298,224 | B2 | 4/2022 | Corbett et al. |
| 11,305,105 | B2 | 4/2022 | Corbett et al. |
| 11,324,619 | B1 | 5/2022 | Yacoby et al. |
| 11,331,421 | B2 | 5/2022 | Kapur |
| 11,524,137 | B2 | 12/2022 | Jahangir |
| 11,547,786 | B2 | 1/2023 | Kapur |
| 11,564,818 | B2 | 1/2023 | Ben-Muvhar |
| 11,612,725 | B2 | 3/2023 | Kapur et al. |
| 11,723,783 | B2 | 8/2023 | Jackson et al. |
| 11,738,131 | B2 | 8/2023 | Kapur |
| 2001/0002445 | A1 | 5/2001 | Vesely |
| 2001/0041858 | A1 | 11/2001 | Ray et al. |
| 2002/0099407 | A1 | 7/2002 | Becker et al. |
| 2002/0115982 | A1 | 8/2002 | Barbut et al. |
| 2003/0023200 | A1 | 1/2003 | Barbut et al. |
| 2003/0153943 | A1 | 8/2003 | Michael et al. |
| 2003/0171771 | A1 | 9/2003 | Anderson et al. |
| 2004/0059276 | A1 | 3/2004 | Maguire et al. |
| 2004/0064090 | A1 | 4/2004 | Keren et al. |
| 2004/0243057 | A1 | 12/2004 | Vinten-Johansen |
| 2005/0055082 | A1 | 3/2005 | Ben Muvhar et al. |
| 2006/0064059 | A1 | 3/2006 | Gelfand et al. |
| 2006/0106449 | A1 | 5/2006 | Ben Muvhar |
| 2006/0106450 | A1 | 5/2006 | Ben Muvhar |
| 2007/0016286 | A1 | 1/2007 | Herrmann et al. |
| 2008/0058591 | A1 | 3/2008 | Saadat et al. |
| 2008/0183036 | A1 * | 7/2008 | Saadat ................. A61B 1/3137 606/41 |
| 2008/0183203 | A1 | 7/2008 | Fitzgerald et al. |
| 2010/0114022 | A1 | 5/2010 | Hirszowicz et al. |
| 2012/0059356 | A1 | 3/2012 | Di Palma et al. |
| 2012/0259215 | A1 * | 10/2012 | Gerrans ............. A61M 25/1011 604/509 |
| 2014/0039537 | A1 * | 2/2014 | Carrison .......... A61B 17/12045 606/191 |
| 2014/0371778 | A1 | 12/2014 | Rudakov et al. |
| 2015/0005809 | A1 | 1/2015 | Ayres et al. |
| 2015/0032087 | A1 | 1/2015 | Shibata et al. |
| 2015/0165173 | A1 * | 6/2015 | Helkowski ....... A61M 25/10184 606/194 |
| 2015/0201944 | A1 * | 7/2015 | Starnes .................. A61B 5/061 606/194 |
| 2016/0206798 | A1 | 7/2016 | Williams et al. |
| 2016/0375230 | A1 | 12/2016 | Lee et al. |
| 2017/0049946 | A1 | 2/2017 | Kapur et al. |
| 2017/0100527 | A1 | 4/2017 | Schwammenthal et al. |
| 2017/0156840 | A1 | 6/2017 | Edmiston et al. |
| 2018/0014829 | A1 | 1/2018 | Tal et al. |
| 2018/0199981 | A1 * | 7/2018 | Sheets .................... A61B 18/02 |
| 2018/0250015 | A1 * | 9/2018 | Koo .................. A61M 25/0108 |
| 2018/0317932 | A1 * | 11/2018 | H'Doubler ....... A61M 25/10182 |
| 2019/0343531 | A1 * | 11/2019 | Tal .................... A61B 17/12022 |
| 2021/0186517 | A1 | 6/2021 | Tal et al. |
| 2022/0039938 | A1 | 2/2022 | Karavany et al. |
| 2024/0164787 | A1 | 5/2024 | Tal et al. |

FOREIGN PATENT DOCUMENTS

| | | |
|---|---|---|
| JP | 2004533290 A | 11/2004 |
| JP | 2010522601 A | 7/2010 |
| JP | 2012502679 A | 2/2012 |
| JP | 2013017833 A | 1/2013 |
| WO | WO-02085443 A1 | 10/2002 |
| WO | WO-2014201434 A2 | 12/2014 |
| WO | WO-2015015314 A2 | 2/2015 |
| WO | WO-2017031231 A1 | 2/2017 |
| WO | WO-2017081561 A1 | 5/2017 |
| WO | WO-2017192912 A1 | 11/2017 |
| WO | WO-2018085890 A1 | 5/2018 |
| WO | WO-2018197983 A1 | 11/2018 |
| WO | WO-2020121309 A1 | 6/2020 |
| WO | WO-2023099984 A1 | 6/2023 |
| WO | WO-2024105526 A1 | 5/2024 |

OTHER PUBLICATIONS

International Search Report issued in PCT/IL2019/051360, date of mailing Apr. 7, 2020, 3 pages.
International Search Report issued in International Application No. PCT/IB2016/055763, date of mailing, Mar. 15, 2017, 5 pages.

* cited by examiner

SYSTEMS, DEVICES, AND METHODS FOR ADJUSTING BLOOD FLOW IN A BODY LUMEN

RELATED APPLICATIONS

This application is a 371 National Stage filing of PCT/IL2019/051360, filed 11 Dec. 2019, which claims benefit of and priority to U.S. provisional patent application No. 62/777,788, filed 11 Dec. 2018, each disclosure of which is herein incorporated by reference in its entirety.

FIELD OF THE DISCLOSURE

Embodiments of the present disclosure generally relate to systems, devices, and methods for any and all of controlling venous pressure, renal function alteration, and urine output (e.g., such as in acute heart failure patients).

BACKGROUND OF THE DISCLOSURE

Congestive heart failure (CHF) is characterized by a progressive loss in the heart's ability to pump blood. Causes range from valvular disease to infection. The affected heart has difficulty in supplying blood to body organs with each contraction. Congestive heart failure symptoms typically include shortness of breath, fluid retention and general fatigue. Most patients with CHF require additional treatments to help manage their disease, typically oral diuretics, inotropes, vasodilators and beta-blockers.

Diuretics help the kidneys rid the body of excess fluid, thereby reducing blood volume and the heart's workload. Inotropes strengthen the heart's pumping action. Vasodilators, such as ACE (angiotension conversion enzyme) inhibitors, cause the peripheral arteries to dilate, making it easier for blood to flow. Beta-blockers slow the heart rate and reduce blood pressure by blocking the effects of adrenaline.

Many congestive heart failure patients eventually experience a rapid deterioration and worsening of symptoms. This sudden worsening of symptoms is called Acute Heart Failure (AHF), and refers to rapid onset or worsening of signs and symptoms of chronic heart failure. It is a life-threatening medical condition requiring urgent treatment that often leads to urgent hospital admission (1M admissions due to AHF annually in the US). Fluid decongestion is the key treatment for AHF, namely high doses of diuretics, a family of drugs designed to increase urine output and sodium secretion. Acutely decompensated heart failure resulting in hospitalization marks a fundamental change in the natural history of the progression of congestive heart failure. Mortality rates in the year following hospitalization for acute heart failure patients are significantly higher than in non-hospitalized patients. Moreover, these patients are particularly prone to readmission, with recurrent hospitalization rates of 50% within 6 months of discharge.

A certain percentage of patients (20-30%) admitted to the hospital for AHF suffer from insufficient response to diuretics and do not achieve rapid fluid removal or complete decongestion. These numbers are supported by published literature and real-world analysis of consecutive admissions. As of today, there are no viable therapies for AHF patients resistant to diuretics. These patients face risks of increased in-hospital mortality, longer hospital stays and high rates of 30-day readmission (23-26%).

SUMMARY OF AT LEAST SOME OF THE EMBODIMENTS OF THE DISCLOSURE

Embodiments of the present disclosure provide systems, devices, and methods for controlling venous pressure, renal function alteration, and urine output, such as in acute heart failure patients, through controlling blood flow in blood vessels (which may also be referred to as body lumen) associated with the kidneys.

In some embodiments, a renal function alteration system is provided and comprises a blood-flow regulation device, which includes an inner tube, an expandable, adjustable member (EAM) coupled to the inner tube, a downstream tip member coupled to a distal portion of the inner tube which is distal to the EAM, the tip member being coupled to a first fluid pressure sensor, and a second fluid pressure sensor coupled to a portion of the inner tube proximal to the EAM. The system can also include a proximal control handle including a controller operatively coupled to the EAM and configured to control expansion of the EAM, a fluid connector coupled to the control handle, and a supply of a therapeutic agent in fluid communication with the fluid connector. The fluid connector can be coupled to the control handle, and upon delivering the EAM to a site near a kidney (for example), the EAM is adjustably expanded so as to effect a desired reduction in blood-flow at the site, and an amount of therapeutic agent is delivered to the implantation site via the fluid connector.

Such embodiments, can further include one and/or another of the following (and in some embodiments, at least two of the following, and in some further embodiments, all of the following) features, structure, functionality, or clarification, leading to yet further embodiments of the present disclosure:

the therapeutic agent is selected from the group consisting of: a diuretic, a blood thinning substance, and an antiplatelet substance, where the blood thinning substance comprises an anticoagulant substance;

the tip member can be conical with a rounded distal-most open tip;

the tip member can be concentric with a distal opening of the EAM;

the first fluid pressure sensor can be coupled to the tip member via a guidewire fluid connector located on a proximal portion of the inner tube;

the first fluid pressure sensor can be disposed in or on the tip member;

the first fluid pressure sensor can comprise a left/first sensor and a right/second sensor;

the tip member and the inner tube can be movable axially with respect to the EAM;

the inner tube can be disposed in an intermediate tube, which can be disposed in a removable outer sheath, and the EAM can be initially disposed in the outer sheath; and a cover impervious to blood flow, which can be arranged to cover at least a portion of the EAM.

In some embodiments, a renal function alteration system is provided comprising a blood-flow adjustment device which comprises an inner tube, an expandable, adjustable member (EAM) coupled to the inner tube, a downstream tip member coupled to a distal portion of the inner tube which is distal to the EAM, the tip member being coupled to a first fluid pressure sensor, and a second fluid pressure sensor coupled to a portion of the inner tube proximal to the EAM. One of skill in the art will appreciate that the blood-flow adjustment device, can be a standalone embodiment (i.e., separate from the system).

Such embodiments (including the stand alone blood-flow adjustment device), can further include one and/or another of the following (and in some embodiments, at least two of the following, and in some further embodiments, all of the following) features, structure, functionality, or clarification, leading to yet further embodiments of the present disclosure:

a proximal control handle including a controller operatively coupled to the EAM and configured to control expansion of the EAM;

a fluid connector coupled to the control handle;

a supply of a therapeutic agent in fluid communication with the fluid connector;

the fluid connector can be coupled to the control handle; and upon delivering the EAM to a site near a kidney, the EAM can be adjustably expanded so as to effect a desired reduction in blood-flow at the site, and optionally, an amount of therapeutic agent can be delivered to the implantation site via the fluid connector.

In some embodiments, a renal function alteration method is provided and comprises providing a blood-flow adjustment system/device according to any disclosed embodiments (e.g., see above), and providing a fluid connector coupled to the control handle. The method also includes delivering the EAM to a site near a kidney, expanding the EAM to a desired amount so as to effect a reduction in blood-flow at the site; and delivering a therapeutic agent to the site via sad fluid connector.

These and other embodiments, advantages, and objects thereof are made even more apparent by the detailed description which follows, and accompanying figures, a brief description of which is set out below.

BRIEF DESCRIPTION OF THE DRAWINGS

At least some of the embodiments of the present disclosure will be understood and appreciated more fully from the following detailed description, taken in conjunction with the drawings, a brief description of which follows.

DETAILED DESCRIPTION OF AT LEAST SOME OF THE EMBODIMENTS

Figure 1:
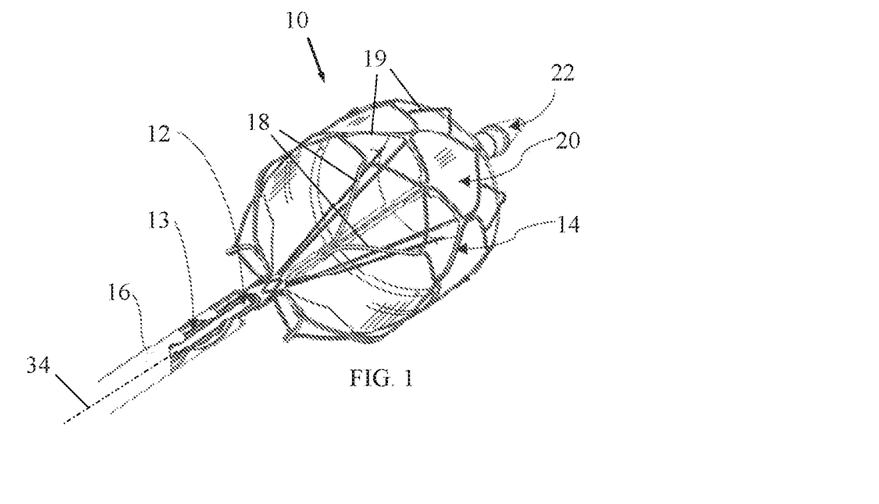
FIG. 1 is an illustration of an adjustable blood-flow device (BFD), according to some embodiments, which includes a multiple shaft or tube construction, an expanding frame, an impervious cover and a distal tip (for example)
Figure 2:
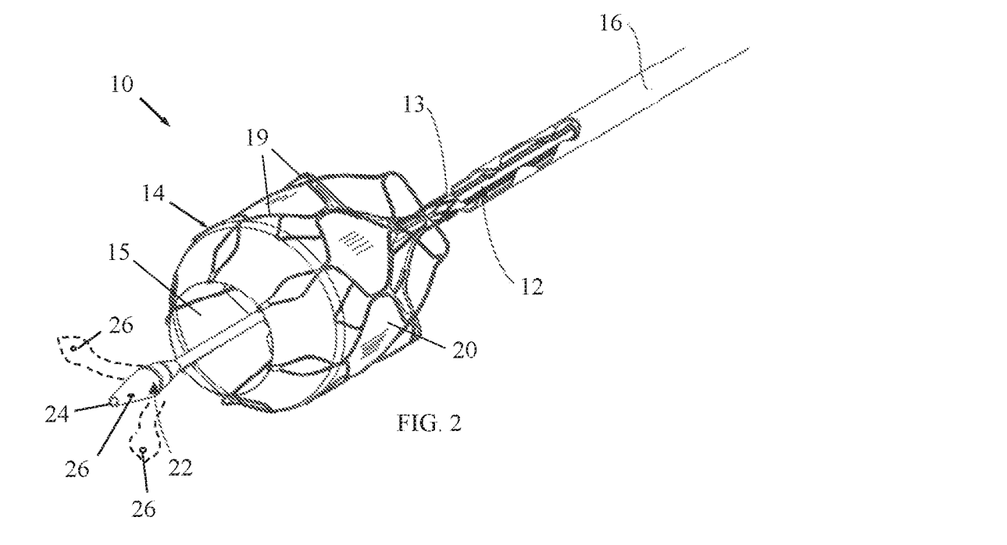
FIG. 2 is an illustration of a distal expanding element of the device of FIG. 1.

Reference is now made to FIGS. 1 and 2, which illustrate an adjustable blood-flow device 10, in accordance with some embodiments of the present disclosure. Accordingly, the device 10 can include an inner tube 12, such as a hollow flexible catheter tube. Inner tube 12 can be disposed in an intermediate tube 13, which in turn can be disposed in an outer sheath 16. An expandable member 14 (which, in some embodiments, is adjustable) is coupled to inner tube 12 and can be initially disposed in outer sheath 16. Member 14 can be deployed by retracting outer sheath 16, which uncovers member 14 and allows it to expand radially outwards.

In some embodiments, member 14 is self-expanding (e.g., constructed of a shape memory material, such as but not limited to, nitinol), or expandable by mechanical means (e.g., wires that push/pull expandable elements), or expandable by fluid means (e.g., hydraulic or pneumatic inflation/deflation of flexible members, such as but not limited to, balloons).

In some embodiments, member 14 expands radially (and/or axially) and conforms to the shape of the body lumen/vessel in which it is deployed. Accordingly, member 14 can be generally cylindrical in shape (although other shapes are within the scope of the disclosure).

In some embodiments, member 14 is constructed of foldable leaflets or struts 18, such as wires or other slender elements, which can be coupled to a flexible frame 19 which includes loops interconnected at different junctures (for example). Such a structure of interconnecting struts 18 and flexible frame 19 can be easily compressed and subsequently expanded to a predetermined shape.

In some embodiments, member 14 can be formed with a distal opening 15 (FIG. 2), which may be referred to as an orifice, through which inner tube 12 protrudes. The foldable leaflets or struts 18 can be coupled to a guidewire 34 (connected to a control knob shown below in FIG. 3), whereas a proximal outer portion of flexible frame 19 of member 14 can be coupled to intermediate tube 13. Similar functionality can be found in associated published PCT no. WO2017081561A1, the entire disclosure of which is herein incorporated by reference.

In some embodiments, the foldable leaflets (which, in some embodiments, include struts 18 or can be separate) can be retracted proximally (by suitable movement of the guidewire) to expand the member 14 from a radially closed position for transition through the body lumen to a radially open position at the target site. The radially open position has a larger diameter that the radially closed state. Alternatively, in some embodiments, the device can be designed such that distal advancement of the foldable leaflets or struts 18 expands member 14 from the radially closed position to the radially open position.

In some embodiments, a covering 20 can cover a portion of member 14, and can comprise a membrane which is impervious to blood flow.

In some embodiments, a downstream tip member 22 can be coupled to a distal portion of inner tube 12. The tip member 22 can be conical with a rounded distal-most open tip 24 that provides little fluid resistance so as not to disturb fluid flow in the body lumen and not cause local turbulences. The downstream tip member 22 can be concentric with the distal opening 15 of member 14, which further ensures that no local turbulences or eddy currents are created and ensure very little pressure drop at the area of the tip member 22.

Figure 3:
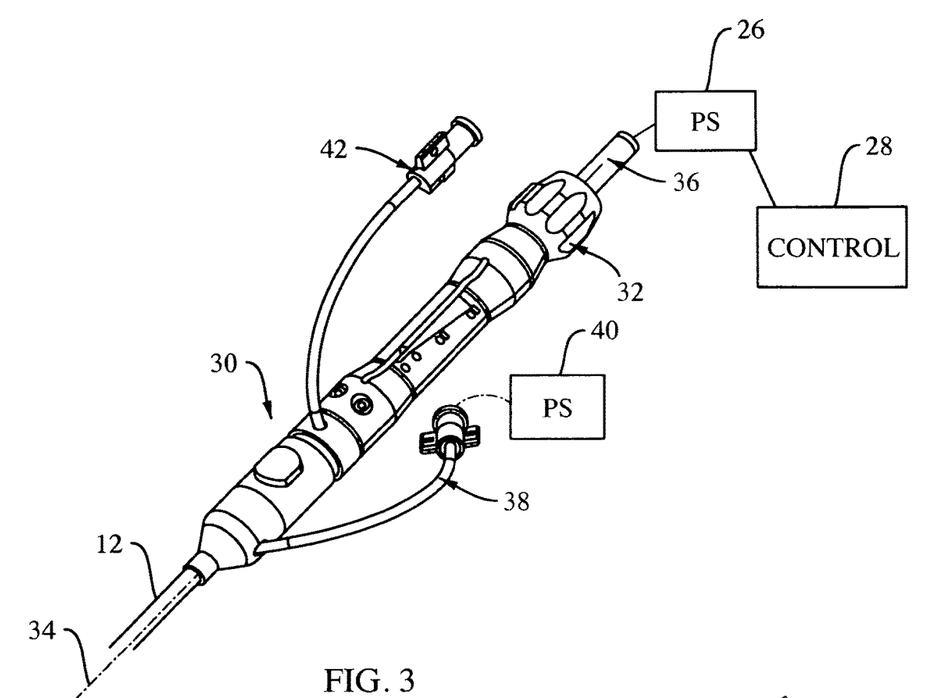
FIG. 3 is an illustration of an external control handle for the device of FIG. 1, according to some embodiments, which includes a control knob, pressure measurement fluid connectors (e.g., luers for upstream and/or downstream) and a therapeutic agent introduction fluid connector (e.g., luer)

Reference is now made to FIG. 3, which illustrates an external control handle for the device according to some embodiments. To this end, all the components at the distal end of device 10 (according to some embodiments) are operatively coupled to a proximal control handle 30, which is located externally from the patient's body during treatment. The distal end of control handle 30 can be coupled to outer sheath 16 in order to move outer sheath 16 proximally to allow member 14 to deploy (expand) radially outwards, or to move outer sheath 16 distally to contract member 14 from its radially open state to its radially closed state.

In some embodiments, device 10 can be introduced using an over-the-wire percutaneous approach (as is known in the field). As mentioned above, guidewire 34 can pass through inner tube 12, where the distal end thereof can reach the distal tip 22 (FIG. 1) and the proximal end of guidewire 34 can exit through a guidewire fluid connector 36 (e.g., luer) at the proximal end of the control handle 30.

A controller 32 (also, in some embodiments, referred to as a control knob, but could also be automated, motorized controller) which can be located on control handle 30 (e.g., proximal end) and can control the degree of flow (i.e., size of the opening upon which blood flows out member 14) of member 14 by controlling the extent of the radial expansion of member 14. In some embodiments, control knob 32 is coupled to guidewire 34 which is coupled to leaflets or struts 18 (FIG. 1). Accordingly, by turning control knob 32, the user can move the foldable leaflets 18 to expand member 14 at the site of the body lumen, thus, adjusting blood flow in the vessel and causing a localized pressure-drop near the location in which member 14 is positioned. The user can control the degree of size of the opening in which blood exits member 14 by suitable turning of control knob 32 (please note, in other embodiments, other kinds of controllers can be employed, mechanical or electrical, instead of the control knob).

In some embodiments, once the distal end of the device is in place in the body lumen, the guidewire 34 can be removed, and a first fluid pressure sensor 26 can be connected to the guidewire fluid connector 36 in the control handle 30. The pressure sensor(s) 26 senses the fluid (blood) pressure at the vicinity of the open tip 24 (FIG. 2), which is the pressure in the blood vessel downstream of the location of the device. The fluid pressure sensor 26 can communicate blood pressure information to external controller 28 for data processing and display.

Figure 4:
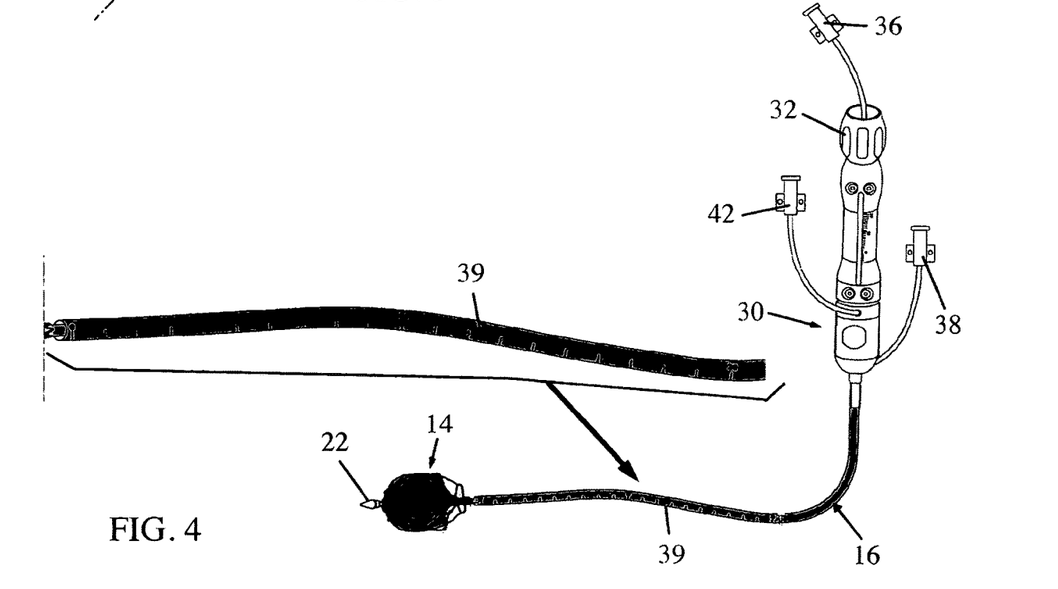
FIG. 4 is an illustration of the device of FIG. 1, including the expanded distal element and the external control handle.

In some embodiments:
  intermediate tube 13 can couple the flexible frame 19 of member 14 for expanding or contracting member 14 (and as mentioned above);
  the flexible frame 19, can be configured to ensure contact between member 14 and the inner vessel wall;
  the gap between the intermediate tube 13 and the inner (guidewire) tube 12 can be used to measure the pressure upstream of the location of member 14;
  a fluid connector 38 (e.g., luer) can be coupled to control handle 30 and is in fluid communication with the intermediate tube 13 via pathways in control handle 30;
  a second fluid pressure sensor 40 can be connected to fluid connector 38 to continuously monitor the upstream pressure near the location of member 14 within the blood vessel. The pressure difference between the upstream and downstream sites can be used to control the degree of flow according to the patient's needs (as before, alternatively, second fluid pressure sensor 40 can be disposed in or on other portions of the device);
  depth or distance markers 39 can be provided, in some embodiments, on device 10 for helping the user in the procedure (see FIG. 4); and/or
  the outer sheath 16, as noted above, is coupled to the distal end of control handle 30.

In some embodiments, a third fluid connector 42 (e.g., luer) can be coupled to the outer sheath hub on control handle 30. The third fluid connector 42 can be used to introduce a therapeutic agent through the outer sheath 16, which, without limitation, the therapeutic agent can be a diuretic and/or a blood thinning substance for reducing the risk of thrombi forming on the distal expanding end during blood flow regulation.

Figure 5:
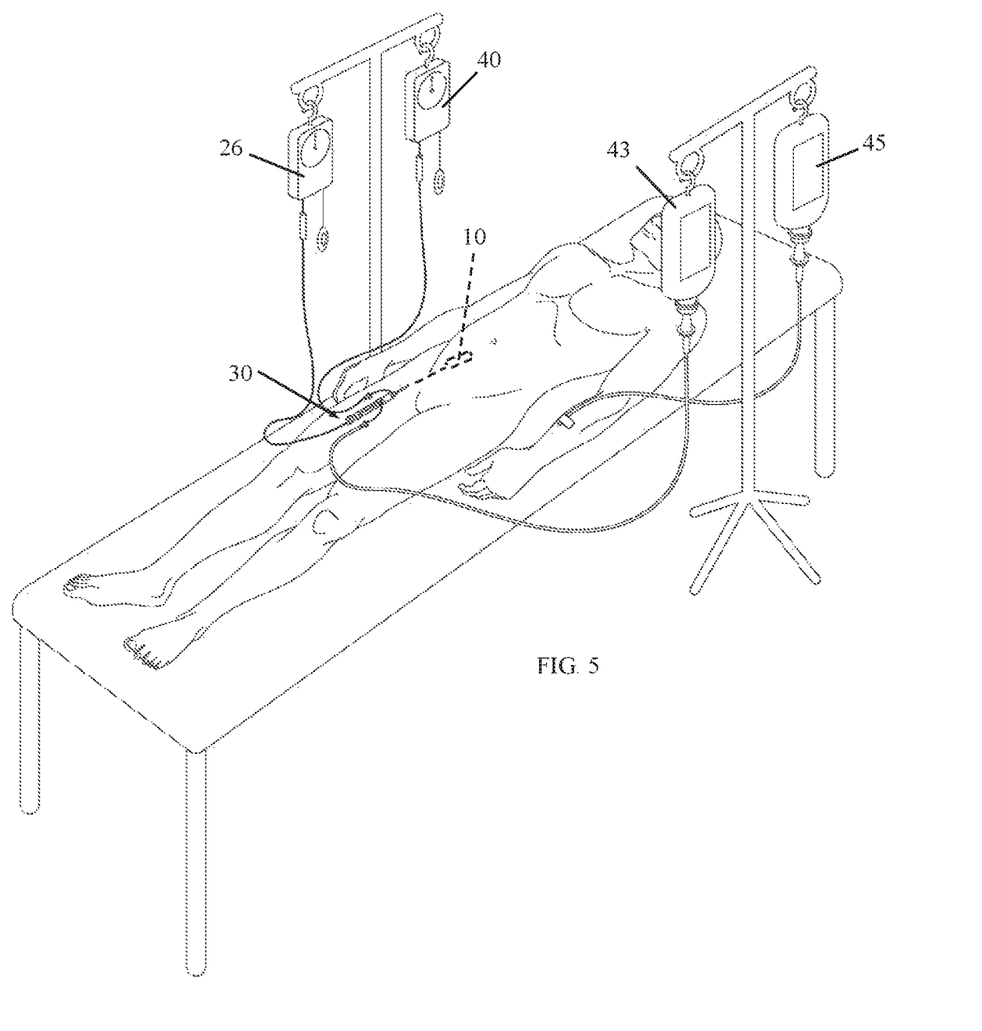
FIG. 5 is an illustration of the device of FIG. 1 after introduction into the patient and coupled to one or more therapeutic agents and pressure sensors.

Reference is now made to FIG. 5, which illustrates the device 10 after being delivered to a site near the renal vasculature, according to some embodiments (FIG. 5 shows the option of bedside delivery). Accordingly, control handle 30 is shown external to device 10 and is coupled to the fluid pressure sensor 26 (and/or circuitry) for continuously monitoring the pressure in the blood vessel downstream of the site and to second fluid pressure sensor 40 (and/or circuitry) for continuously monitoring the upstream pressure near the site. The control handle 30 is in fluid communication with one or more therapeutic agents, such as a blood thinning substance 43 and/or a diuretic 45.

In some embodiments, a therapeutic agent 43 (e.g., a blood thinning substance) can be an antiplatelet substance. Antiplatelet therapy has been shown to reduce clinical ischemic events and improve outcomes for acute coronary syndrome patients. Non-limiting examples of antiplatelet substances include GPIIb/IIIa inhibitors, dipyridamole, (low-dose) aspirin (acetylsalicylic acid), a selective COX-2 or nonselective COX-1/COX-2 inhibitor, or a ADP receptor inhibitor, such as a thienopyridine (e.g., clopidogrel, ticlopidine or prasugrel), elinogrel or ticagrelor, or a thrombin receptor antagonist such as vorapaxar, or analogs or derivatives or combinations thereof. Thienopyridines such as clopidogrel irreversibly inhibit $P2Y_{12}$ receptors, which play an active role in platelet activation. In the normal state, when blood vessels are damaged, platelet activation mediated by $P2Y_{12}$ receptors play an important role to arrest bleeding at the site of injury. In a diseased state, platelet activation leads to vascular obstruction and ischemic damage. Thus, $P2Y_{12}$ receptor antagonists play a key role in antiplatelet therapy in assisting to prevent coronary artery disease and for the immediate treatment of acute coronary syndrome and percutaneous coronary intervention.

In some embodiments:
  the therapeutic agent 43 (blood thinning substance) can be an anticoagulant substance, such as but not limited to, heparin, warfarin, rivaroxaban, dabigatran, apixaban, edoxaban, enoxaparin, or fondaparinux; and
  the diuretic 45 can include, without limitation, thiazide diuretics (e.g., chlorthalidone, hydrochlorothiazide, metolazone, indapamide), loop diuretics (e.g., torsemide, furosemide, bumetanide), and/or potassium-sparing diuretics (e.g., amiloride, triamterene, spironolactone eplerenone).

In some embodiments, the device can also include a controllable device having continuous pressure measurement across the device. For example, as shown in broken lines in FIG. 2, alternatively fluid pressure sensor 26 can be disposed in or on tip member 22. The fluid pressure sensor 26 can be a wireless blood pressure sensor, available from many manufacturers, which wirelessly communicates blood pressure information to circuitry 27 and/or external controller 28 (FIG. 3). Two fluid pressure sensors 26 can be used: a left sensor and a right sensor (and even in some embodiments, also a central censor) for measuring the blood pressure in the vicinity of the left and right renal veins, respectively (see FIG. 2). The pressure sensors can be at left, central, and/or right portions of the tip member 22; alternatively, a bifurcated tip member (shown in broken lines) can be employed. In another alternative, tip member 22 with inner tube 12 can be movable axially with respect to member 14. In this manner, the user can adjust the distance tip member 22 protrudes from member 14 to suit different anatomical geometries.

Figure 6:
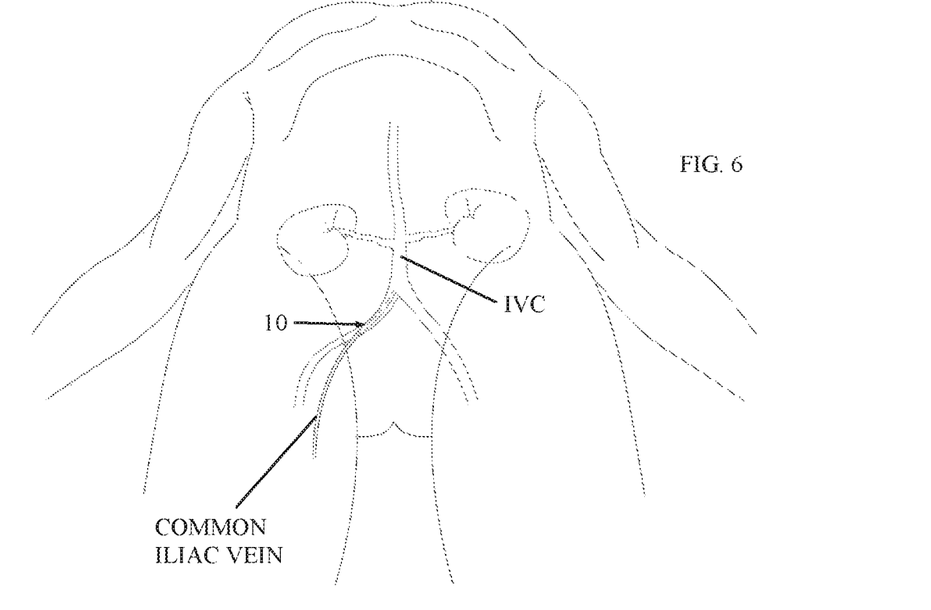
FIG. 6 is an illustration of the introduction of the device of FIG. 1 through a body lumen (e.g., shown in this example with the catheter system is introduced in the common iliac vein)
Figure 7:
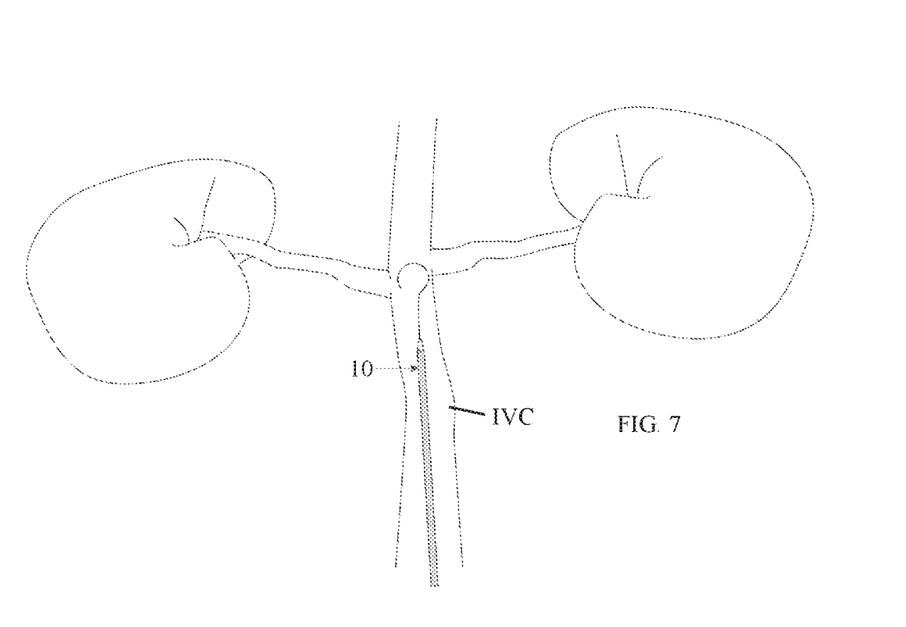
FIG. 7 is an illustration of a distal end of the device of FIG. 1 being located at a treatment location/site (e.g., shown in this example in the inferior vena cava (IVC) near the junction to the left and right renal veins)

Reference is now made to FIG. 6, which illustrates delivering the device 10 via the common iliac vein towards the inferior vena cava (IVC), according to some embodiments. In FIG. 7, a distal end of device 10 is being located at a site; in this example, in the IVC near the junction to the left and right renal veins.

Figure 8:
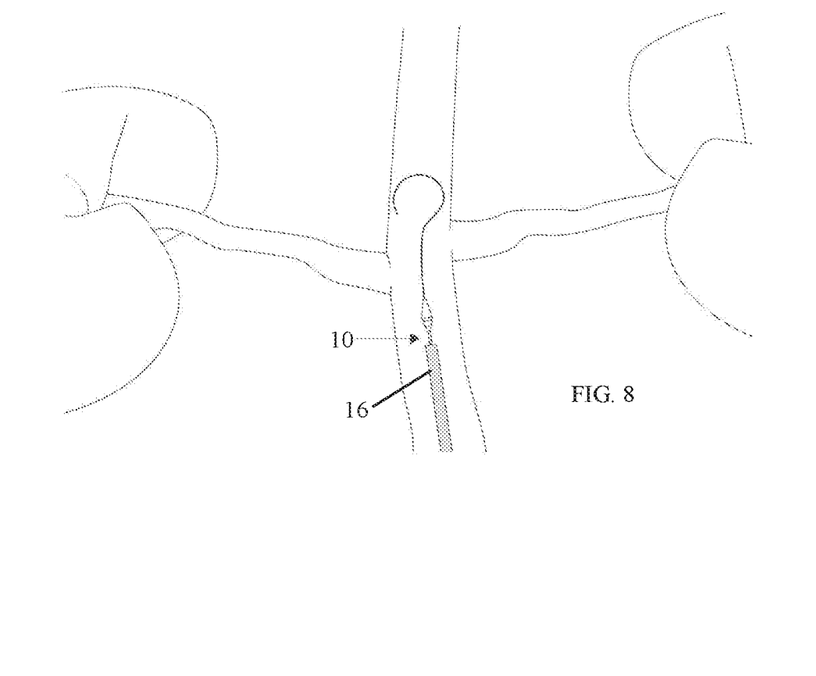
FIG. 8 is an illustration of the starting of unsheathing of an outer shaft of the device of FIG. 1.

Reference is now made to FIG. 8, which illustrates the starting of the unsheathing of the outer sheath 16 of device 10, according to some embodiments.

Figure 9:
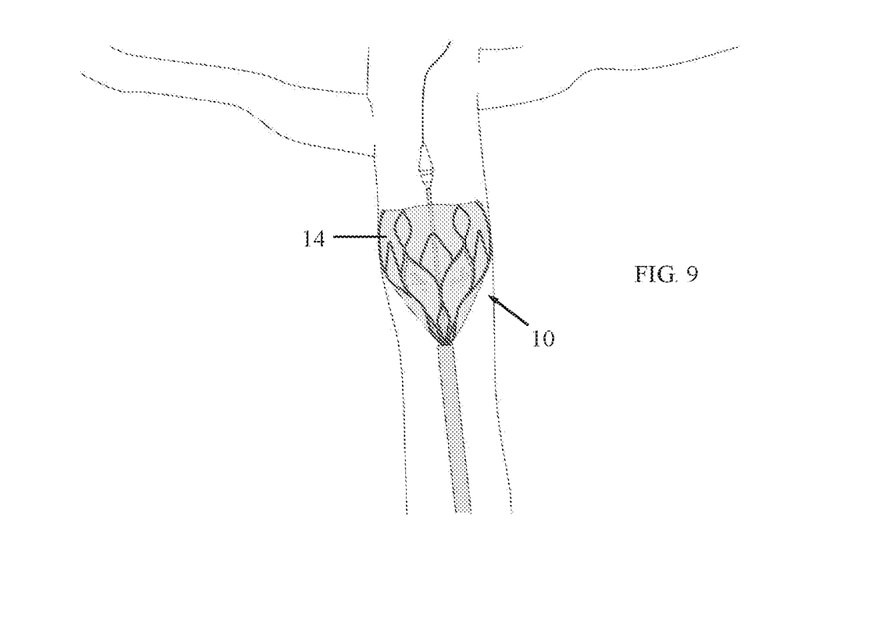
FIG. 9 is an illustration of the device of FIG. 1 in its fully radially expanded orientation, in which a distal element is not yet effected an adjustment of blood flow in the body lumen.

Reference is now made to FIG. 9, which illustrates device 10 in its fully radially expanded orientation, according to some embodiments. The distal member 14 is not yet affecting flow in the body lumen.

Figure 10:
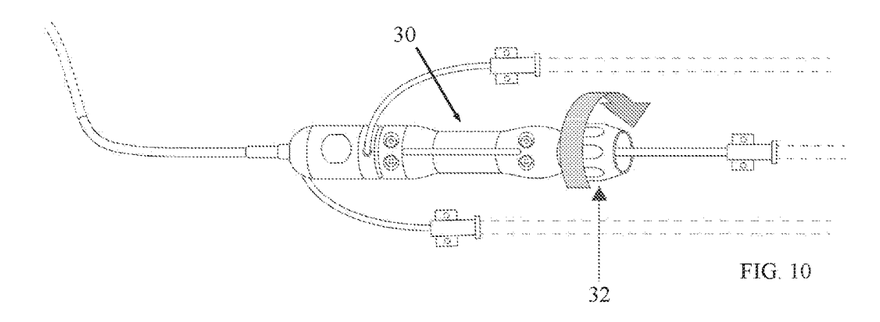
FIG. 10 is an illustration of a control knob being rotated on a control handle, according to some embodiments, associated with the device of FIG. 1, which causes foldable leaflets in the distal end of the device (not shown here) to be pulled radially inward, causing an adjustment of flow in the body lumen, by partially blocking a portion of the flow.

Reference is now made to FIG. 10, which illustrates control knob 32 being rotated on control handle 30, which causes radially-outward expansion of the member to eventually cause a change in flow in the body lumen, according to some embodiments.

Figure 11A:
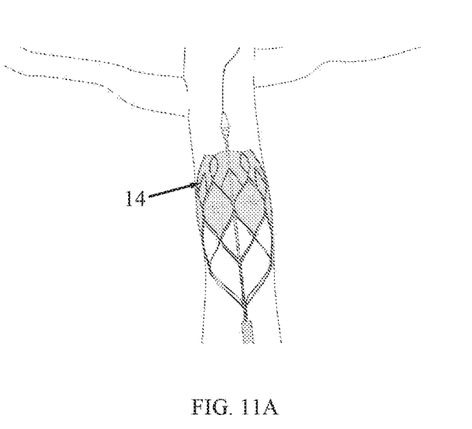
FIGS. 11A and 11B are illustrations of the distal element of the device of FIG. 1, respectively in partially and fully closed positions, with foldable leaflets pulled radially inward, thereby respectively adjusting blood flow therein, up to and including substantially blocking flow of the body lumen (i.e., obstructing a substantial portion thereof, in some embodiments).
Figure 11B:
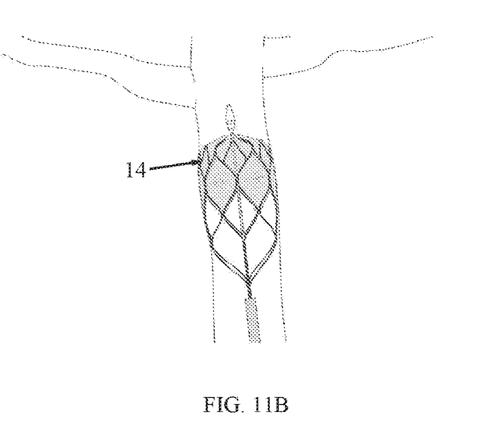

Reference is now made to FIG. 11A, which illustrates the member 14 in a partially expanded position and FIG. 11B which illustrates the member 14 in a fully expanded position, thereby substantially closing the flow in the body lumen, according to some embodiments (and in some embodiments, closing the flow).

In some embodiments, placement of device 10 in the inferior vena cava, caudal to the inlet of the renal veins, effects a change in flow and creates a lower pressure zone in the area thereof, thereby increasing the pressure gradient on the kidneys and increasing urine output. The controllable device catheter can be designed for bedside delivery, which minimizes treatment time and recovery. Once a desired change in flow is achieved, diuretics can be given to the patient. The combination of the change in flow and the diuretics can improve renal function, increase patient urine output and help extract extraneous fluid from the interstitial tissue.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be an example and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of claims supported by the subject disclosure and equivalents thereto, and inventive embodiments may be practiced otherwise than as specifically described and claimed. Inventive embodiments of the present disclosure are directed to each individual feature, system, article, material, kit, step, and/or method described herein. In addition, any combination of two or more such features, systems, articles, materials, kits, steps, and/or methods, if such features, systems, articles, materials, kits, steps, and/or methods are not mutually inconsistent, is included within the inventive scope of the present disclosure.

Embodiments disclosed herein may also be combined with one or more features, as well as complete systems, devices and/or methods, to yield yet other embodiments and inventions. Moreover, some embodiments, may be distinguishable from the prior art by specifically lacking one and/or another feature disclosed in the particular prior art reference(s); i.e., claims to some embodiments may be distinguishable from the prior art by including one or more negative limitations.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Any and all references to publications or other documents, including but not limited to, patents, patent applications, articles, webpages, books, etc., presented anywhere in the present application, are herein incorporated by reference in their entirety. Moreover, all definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is currently claimed is:

1. A renal function alteration system comprising:
a blood-flow regulation device comprising:
an inner tube,
an expandable, adjustable member (EAM) coupled to the inner tube, the EAM comprising:
a proximal end and a distal end;
a cylindrical section positioned between the proximal and distal end of the EAM;
a plurality of radially inwardly foldable leaflets connected between a distal end of the cylindrical section and an adjustable opening at the distal end of the EAM; and
a blood impervious cover configured to cover at least a portion of a distal end of the cylindrical section and an outer surface of the foldable leaflets such that blood flows through the cylindrical section and out the adjustable opening;
wherein the inner tube passes through the cylindrical section of the adjustable opening;
a downstream tip member coupled to a distal portion of the inner tube which is distal to the EAM, the downstream tip member being coupled to a first fluid pressure sensor, and
a second fluid pressure sensor coupled to the blood flow regulation device proximal to the EAM;
a proximal control handle including a controller operatively coupled to the foldable leaflets and configured to control the size of the adjustable opening;
a fluid connector coupled to the proximal control handle; and
a supply of a therapeutic agent in fluid communication with the fluid connector,
wherein upon delivering the EAM to a site near a kidney, the adjustable opening of the EAM is adjusted to effect a desired reduction in blood-flow at the site, and an amount of the supply of therapeutic agent is delivered to the site via the fluid connector.

2. The renal function alteration system of claim 1, wherein the therapeutic agent is selected from a group consisting of: a diuretic, a blood thinning substance, and an antiplatelet substance.

3. The renal function alteration system of claim 2, wherein the blood thinning substance comprises an anticoagulant substance.

4. The renal function alteration system of claim 1, wherein the downstream tip member is:
conical with a rounded distal-most open tip; and/or
concentric with a distal opening of the EAM.

5. The renal function alteration system of claim 1, wherein the first fluid pressure sensor is;
coupled to the downstream tip member via a guidewire fluid connector located on a proximal portion of the inner tube,
disposed in or on the tip member, and
comprises a first lateral fluid pressure sensor and a second lateral fluid pressure sensor.

6. The renal function alteration system of claim 1, wherein the first fluid pressure sensor is disposed in or on a distal portion of the downstream tip member, and comprises a first lateral fluid pressure sensor and a second lateral fluid pressure sensor.

7. The renal function alteration system of claim 1, wherein the downstream tip member and the inner tube are movable axially with respect to the EAM.

8. The renal function alteration system of claim 1, wherein:
the inner tube is disposed in an intermediate tube, which is disposed in a removable outer sheath,
the EAM is initially disposed in the outer sheath, and/or
the renal function alteration system further comprises a cover impervious to blood flow, arranged to cover at least a portion of the EAM.

9. A renal function alteration system comprising a blood-flow regulation device comprising:
an inner tube,
an expandable, adjustable member (EAM) coupled to the inner tube, the EAM comprising:
a proximal end and a distal end;
a cylindrical section positioned between the proximal and distal end of the EAM;

a plurality of radially inwardly foldable leaflets connected between a distal end of the cylindrical section and an adjustable opening at the distal end of the EAM; and a blood impervious cover configured to cover at least a portion of a distal end of the cylindrical section and an outer surface of the foldable leaflets such that blood flows through the cylindrical section and out the adjustable opening; and a downstream tip member coupled to a distal portion of the inner tube which is distal to the EAM, wherein:

the downstream tip member is coupled to a first fluid pressure sensor, and a second fluid pressure sensor is coupled to the blood flow regulation device proximal to the EAM.

10. The renal function alteration system of claim 9, further comprising a proximal control handle including a controller operatively coupled to the foldable leaflets and configured to control the size of the adjustable opening.

11. The renal function alteration system of claim 9, further comprising a fluid connector coupled to a proximal control handle.

12. The renal function alteration system of claim 9, further comprising a supply of a therapeutic agent in fluid communication with a fluid connector.

13. The renal function alteration system of claim 9, wherein a fluid connector coupled to a proximal control handle, and upon delivering the EAM to a site near a kidney, the foldable leaflets are adjusted so as to effect a desired reduction in blood-flow at the site, and an amount of therapeutic agent is delivered to the site via a fluid connector.

14. A renal function alteration method comprising:
providing:
a blood-flow regulation device according to claim 9, and
the fluid connector coupled to the proximal control handle,
delivering the EAM to the site near a kidney;
adjusting the size of the adjustable opening so as to effect the desired reduction in blood-flow at the site; and
delivering the therapeutic agent to the site via said fluid connector.

15. A blood-flow regulation device comprising:
an inner tube,
an expandable, adjustable member (EAM) coupled to the inner tube, the EAM comprising:
a proximal end and a distal end;
a cylindrical section positioned between the proximal and distal end of the EAM;
a plurality of adjustable, radially inwardly foldable leaflets connected between a distal end of the cylindrical section and an adjustable opening at the distal end of the EAM; and
a blood impervious cover configured to cover at least a portion of a distal end of the cylindrical section and an outer surface of the foldable leaflets such that blood flows through the cylindrical section and out the adjustable opening; and
a downstream tip member coupled to a distal portion of the inner tube which is distal to the EAM, the downstream tip member being coupled to a first fluid pressure sensor, and a second fluid pressure sensor coupled to the blood flow regulation device proximal to the EAM.

16. The blood-flow regulation device of claim 15, wherein the adjustable opening is configured to be controlled via a proximal control handle located outside a patient's body.

17. The blood-flow regulation device of claim 16, wherein the proximal control handle includes a controller operatively coupled to the foldable leaflets to control expansion of the adjustable opening.

18. The blood-flow regulation device of claim 15, wherein the downstream tip member is conical with a rounded distal-most open tip.

19. The blood-flow regulation device of claim 15, wherein the downstream tip member is concentric with a distal opening of the EAM.

20. The blood-flow regulation device of claim 15, wherein the first fluid pressure sensor is coupled to the downstream tip member via a guidewire fluid connector located on a proximal portion of the inner tube.

21. The blood-flow regulation device of claim 15, wherein the first fluid pressure sensor is disposed in or on the downstream tip member.

22. The blood-flow regulation device of claim 15, wherein the first fluid pressure sensor comprises a first lateral fluid pressure sensor and a second lateral fluid pressure sensor.

23. The blood-flow regulation device of claim 15, wherein the downstream tip member and the inner tube are movable axially with respect to the EAM.

24. The blood-flow regulation device of claim 15, wherein the inner tube is disposed in an intermediate tube, which is disposed in a removable outer sheath, and the EAM is initially disposed in the outer sheath.

* * * * *